United States Patent [19]

Davis

[11] Patent Number: 4,663,318

[45] Date of Patent: May 5, 1987

[54] METHOD OF TREATING ALZHEIMER'S DISEASE

[76] Inventor: Bonnie Davis, 17 Seacrest Dr., Huntington, N.Y. 11743

[21] Appl. No.: 819,141

[22] Filed: Jan. 15, 1986

[51] Int. Cl.$^4$ ............................................. A61K 31/55
[52] U.S. Cl. ................................................. 514/215
[58] Field of Search ........................................ 514/215

[56] References Cited

PUBLICATIONS

Chem. Abst. (81)-72615z (1974).
Chem. Abst. (86)-115157z (1977).
Horshenson et al. J. Med. Chem. vol. 29, No. 7, 7/86, pp. 1125-1130.
Kendall et al., J. Chem. & Hospital Pharmacol., (1985) 10-327-330.
S. Chaplygina et al., J. of Highest Nervous Activity vol. XXIV 1976 Issue 5, pp. 1-4.
Krause, J. of Highest Nervous Activity, vol. XXII, 1974, Issue 4.

*Primary Examiner*—Stanley J. Friedman
*Attorney, Agent, or Firm*—Ladas & Parry

[57] ABSTRACT

Alzheimer's disease may be treated with galanthamine.

7 Claims, No Drawings

METHOD OF TREATING ALZHEIMER'S DISEASE

GENERAL FIELD OF THE INVENTION

The present invention relates to a novel method of treating Alzheimer's disease and more particularly to a treatment using galanthamine.

BACKGROUND ART

Galanthamine and acid addition salts thereof have, for many years, been known to have anticholinesterase properties. Cozanitis in Anaesthesia 29 163-8 (1974) describes the effect of galanthamine hydrobromide on plasma cortisol of patients receiving relaxant anaesthesia and Cozanitis et al in Acta Anesth. Scand. 24:166-168 (1980) describe the effect of galanthamine on plasma ACTH values during anaethesia. These studies showed an increase in both plasma cortisol and plasma ACTH when galanthamine was administered to patients together with atropine.

Il'yuchenok et al (Chemical Abstracts 70 36296K describe the appearance of θ-rhythm on an electroencephalogram when galanthamine is administered intravenously to rabbits.

Increase in short-term memory in dogs by use of galanthamine is described by Krauz in Chemical Abstracts 81 72615Z.

The antagonistic effect of galanthamine to scopolamine-induced amnesia in rats is described by Chaplygina et al in Chemical Abstracts 86 115157Z, and in Zhurnal Vysshei Nervnoi Deiatelnosti imeni P. Pavlova (MOSKVA) 26:1091-1093, 1976.

Alzheimer's disease, presenile dementia, causes much distress not only to those suffering from the disease, but also those who are close to them. The custodial care of advanced victims of the disease is a tremendous expense to society. At present, there is no effective means of improving the functional status of persons with the disease.

It is an object of the present invention to improve the cognitive function of patients with Alzheimer's disease.

SUMMARY OF THE INVENTION

A method for treating Alzheimer's disease and related dementias which comprises administering to mammals, including humans, an effective Alzheimer's disease cognitively-enhancing amount of galanthamine or a pharmaceutically-acceptable acid addition salt thereof. A radioactively-labelled form of the molecule may also serve as a diagnostic test for Alzheimer's disease.

DETAILED DESCRIPTION OF THE INVENTION

Galanthamine can be administered in any convenient chemical or physcial form. For example, it may be administered as its hydrobromide, hydrochloride, methylsulfate or methiodide.

Galanthamine or its pharmaceutically-acceptable acid addition salts may be administered to a patient suffering from Alzheimer's disease orally or by subcutaneous or intravenous, injection, or intracerebroventricularly by means of an implanted reservoir. It may be necessary to begin at lower doses than are ultimately effective.

Galanthamine and its acid addition salts form crystals. They are in general only sparingly soluble in water at room temperature and so injectible compositions are normally in the form of an aqueous suspension. If necessary, pharmaceutically-acceptable suspension aids may be employed. Typically, such a suspension will be employed at a concentration of 1-50 mg/ml more commonly 5-40 mg/ml, for example, 5-30 mg/ml or 10-40 mg/ml, typically 20-30 mg/ml of galanthamine. Typical dosage rates when administering galanthamine by injection are in the range 5-1,000 mg per day depending upon the patient. For example, divided doses in the range 0.5-5 mg/kg body weight per day may prove useful. Typically, one might administer a dosage of 50-300 mg per day to a patient of a body weight of 40-100 kg, although in appropriate cases such dosages may prove useful for patients having a body weight outside this range. In other cases, dosages as low as 10 mg and as high as 500 mg may be appropriate for persons in this body weight range.

Galanthamine or its pharmaceutically-acceptable acid addition salts may also be administered orally, for example, as an aqueous suspension or a solution in aqueous ethanol or as a solid such as a tablet or capsule. Suspensions or solutions for oral administration are typically of about the same concentration as those used for injections. However, it may be desirable when administering the drug orally to use a higher dosage rate than when administering it by injection. For example, dosages up to 2000 mg per day may be used, such as dosages in the range 100-600 mg per day. In preparing such tablets or capsules, standard tablet or capsulemaking techniques may be employed. The dosage rate of galanthamine or its pharmaceutically-acceptable salt will normally be in the same range as for oral administration of a liquid. If desired, a pharmaceutically-acceptable carrier such as starch or lactose may be used in preparing galanthamine tablets. Capsules may be prepared using soft galatine as the encapsulating agent. If desired, such capsules may be in the form of sustained release capsules wherein the main capsule contains microcapsules of galanthamine which release the contents over a period of several hours thereby maintaining a constant level of galanthamine in the patient's blood stream.

The following test provides a good animal model for Alzheimer's disease in humans: A selective lesion is placed in a subcortical nucleus (nucleus basalis of Meynert) with a resultant cortical cholinergic deficiency, similar in magnitude to that seen in early to moderate stage Alzheimer's disease. Numerous behavioral deficits, including the inability to learn and retain new information, characterizes this lesion. Drugs that can normalize these abnormalities would have a reasonable expectation of efficacyin Alzheimer's disease. Haroutunian, V, Kanof P, Davis, KL: Pharmacological alleviations of cholinergic-lesion-induced memory defects in rats. Life Sciences 37:945-952, 1985.

The following specific formulations may find use in treatment of Alzheimer's disease:

Tablets or capsules containing 5, 10 and 25 mg galanthamine hydrobromide to be taken four times a day, or a sustained-release preparation delivering an equivalent daily dose.

Parenteral solution containing 5 mg/ml.

Liquid formulation for oral administration available in 5 mg/5 ml and 25 mg/5 ml concentration.

There have been reports that galanthamine can cause cardiac arrythmias. In such cases, it may be desirable to administer galanthamine in conjunction with another drug such as propanthelinbromide to control such arrythmias.

I claim:

1. A method of treating Alzheimer's disease and related dementias which comprises administering to a patient suffering from such a disease a therapeutically effective amount of galanthamine or a pharmaceutically-acceptable acid addition salt thereof.

2. A method according to claim 1, wherein the administration is parenteral at a daily dosage of 5-1,000 mg of galanthamine or a pharmaceutically-acceptable acid addition salt thereof.

3. A method according to claim 2, wherein said dosage rate is 50-300 mg per day.

4. A method according to claim 1, wherein said administration is oral and is in the range 10-2000 mg per day.

5. A method according to claim 4, wherein said dosage rate of 100-600 mg per day.

6. A method according to claim 1, wherein galanthamine is administered at a dosage rate of 0.1 to 4 mg/kg body weight of a patient, parenterally.

7. A method according to claim 1, wherein galanthamine is administered intracerebroventricularly via an implanted reservoir at a dosage rate of 0.01 to 5.0 mg/kg day.

* * * * *